United States Patent
Tegenfeldt et al.

(10) Patent No.: US 10,434,512 B2
(45) Date of Patent: *Oct. 8, 2019

(54) METHOD FOR THE MAPPING OF THE LOCAL AT/GC RATIO ALONG DNA

(71) Applicants: Jonas Tegenfeldt, Lund (SE); Walter Reisner, Montreal (CA); Henrik Flyvbjerg, Charlottenlund (DK)

(72) Inventors: Jonas Tegenfeldt, Lund (SE); Walter Reisner, Montreal (CA); Henrik Flyvbjerg, Charlottenlund (DK)

( * ) Notice: Subject to any disclaimer, the term of this patent is extended or adjusted under 35 U.S.C. 154(b) by 384 days.

This patent is subject to a terminal disclaimer.

(21) Appl. No.: 15/462,023

(22) Filed: Mar. 17, 2017

(65) Prior Publication Data

US 2017/0252743 A1    Sep. 7, 2017

Related U.S. Application Data

(63) Continuation of application No. 13/123,395, filed as application No. PCT/SE2009/000444 on Oct. 9, 2009, now Pat. No. 9,597,687.

(30) Foreign Application Priority Data

Oct. 10, 2008   (SE) ..................... 0802134

(51) Int. Cl.
*C12Q 1/68* (2018.01)
*B01L 3/00* (2006.01)
*C12Q 1/6816* (2018.01)
*B01L 7/00* (2006.01)
*G01N 21/64* (2006.01)

(52) U.S. Cl.
CPC ...... *B01L 3/502761* (2013.01); *C12Q 1/6816* (2013.01); *B01L 7/00* (2013.01); *B01L 2200/0663* (2013.01); *B01L 2300/0877* (2013.01); *B01L 2300/1805* (2013.01); *B01L 2300/1833* (2013.01); *B01L 2300/1861* (2013.01); *G01N 21/6458* (2013.01); *Y10T 436/143333* (2015.01)

(58) Field of Classification Search
None
See application file for complete search history.

(56) References Cited

U.S. PATENT DOCUMENTS 8,951,731 B2 *   2/2015  Drmanac ............. C12Q 1/6825
                                              435/6.12

OTHER PUBLICATIONS

Jo et al., A single-molecule barcoding system using nanoslits for DNA analysis, Proc Natl Acad Sci U S A. Feb. 20, 2007;104(8): 2673-8. Epub Feb. 12, 2007.*
Riehn et al., Restriction mapping in nanofluidic devices, Proc Natl Acad Sci U S A. Jul. 19, 2005;102(29):10012-6. Epub Jul. 6, 2005.*
Chan et al., DNA Mapping Using Microfluidic Stretching and Single-Molecule Detection of Fluorescent Site-Specific Tags, Genome Res. Jun. 2004; 14(6): 1137-1146.*

* cited by examiner

*Primary Examiner* — Aaron A Priest
(74) *Attorney, Agent, or Firm* — Rosenberg, Klein & Lee

(57) ABSTRACT

The invention relates to a method for analysis of the AT/GC ratio of DNA by stretching the DNA in nanochannels and performing melting mapping of the AT/GC ratio along the DNA molecule.

9 Claims, 17 Drawing Sheets

METHOD FOR THE MAPPING OF THE LOCAL AT/GC RATIO ALONG DNA

CROSS-REFERENCE TO RELATED APPLICATIONS

This patent application claims the benefit of priority as a continuation of U.S. Ser. No. 13/123,395 filed Apr. 8, 2011, currently pending, entitled "Method for the Mapping of the Local AT/GC Ratio along DNA", which itself claims priority as a 371 National Phase Patent Application of PCT/SE2009/000,444 filed Oct. 9, 2009 entitled "Method for the Mapping of the Local AT/GC Ratio along DNA", which itself claims priority from Swedish Patent Application No. 0802134-7 filed Oct. 10, 2008 entitled "Method for the Mapping of the Local AT/GC Ratio along DNA", the entire contents of each being included herein by reference.

FIELD OF INVENTION

The invention relates to a method for the mapping of the local AT/GC ratio along the DNA as well as a nanochannel device to be used in said method.

BACKGROUND OF THE INVENTION

DNA mapping takes place using a variety of techniques, which give coarsegrained information on the genome. These techniques are based on sequence specific probes such as in DNA arrays or in fluorescence in-situ hybridization (FISH) with resolution of ~50 kbp. They can also be based on restriction enzymes that cut the DNA at specific sequences with resolution ~5 kbp. A common limitation for these techniques is that solely the sequences present in the test can be analysed. Chromosomal banding such as G-banding of metaphase chromosomes circumvents the need for sequence specific probes but with a poor resolution of ~5 Mbp.

Array comparative genomic hybridisation (CGH) uses DNA arrays to map out the entire genome, specifically looking for copy number variations (CNV). The arrays can be based on BAC clones, cDNA, oligonucleotides or PCR products. The unknown DNA is stained in one colour and mixed with the known DNA stained in another colour. The DNA mixture is allowed to hybridize to the DNA in the array and the result is an array of differently coloured spots. The ratio of the intensities of the two colours in each spot gives information on the CNV. If the intensities of the spots are equal there is no change in copy number. The technique requires hours or days of preparation and several hours to a whole day for the hybridization reactions. Array preparation is complex. Furthermore, the technique is only sensitive to sequences that are represented in the array. It is useful for studies of structural variations that involve a net change in copy numbers. Thus it does not detect balanced translocations and inversions. The resolution is determined by the length and density of probes with a resolution better than 100 kbp. Single-cell array CGH has been demonstrated with a resolution of 1-10 Mbp.

Melting of DNA has been used to detect single basepair variations in genomic DNA using for example constant denaturant gel electrophoresis (CDGE) and denaturing gradient gel electrophoresis (DGGE). Both work well for short stretches of DNA but not for long chromosomal DNA. Scanning electron microscopy has been used to study the melting pattern on a longer length scale [Borovik, A. S.; Kalambet, Y. A.; Lyubchenko, Y. L.; Shitov, V. T.; Golovanov, E. I. Nuc. Acid. Res. 1980, 8, 4165-4184. R. H. Austin, Proc. Natl. Acad. Sci. USA 1Ol, 10979 (2004)]. This is however a cumbersome and time-consuming technique which requires expensive equipment and specialized training, and it does not lend itself to integration with Lab on a Chip based techniques. It also precludes real-time measurements of melting in aqueous solutions.

Even though there are a large number of ways to analyse DNA, some of them mentioned above, none of the techniques available today present a method wherein it is possible to study the patterns of local AT/GC ratio along large single DNA molecules in an easy, fast and non-expensive way together with good resolution and with a potential of measurements on a single-cell basis.

SUMMARY OF THE INVENTION

The invention relates to a method wherein it for the first time is possible to obtain a pattern that corresponds to the map of the local AT/GC ratio along the DNA in a simple manner and with short preparation and measurement times. The resulting map of the local AT/GC ratio constitutes a "barcode" pattern along the DNA that can be used to identify patches of interest along genomic DNA and thereby identify structural variations such as deletions, translocations, insertions, inversions and copy number variations on a scale ranging from roughly 1 kbp and up, which is especially relevant in light of recent awareness of the significance of these types of variations. The method is thus limited to mapping and cannot be used to directly sequence the DNA by imaging one nucleotide at the time. The technique complements existing clinical techniques for DNA analysis (chromosomal analysis, FISH, micro arrays, sequencing) through its simplicity, low cost, high speed and lack of any necessary specific labels. The length scales that can be probed exceed what has been studied using existing melting mapping procedures and can apply to DNA molecules ranging at least from kbp to Mbp or even longer with dedicated channel designs and stretching schemes. In a first aspect the invention relates to a method for the mapping of the local AT/GC ratio along the DNA, providing DNA having a length of 1 kbp or more, staining said DNA with a fluorescent dye, denaturating said DNA and obtaining a pattern showing the distribution of the nucleotides.

In a second aspect the invention relates to a nanochannel device comprising at least one nanochannel having two first inlets and a second outlet and a heating source for heating said nanochannel. The nanochannel device may comprise at least one channel having a length of from roughly 10 microns to several hundreds of microns or even longer and with a channel cross-section that is typically 30 nm×30 nm up to up 900 nm×900 nm or more provided the channel diameter is less than the size (radius of gyration) of the DNA blob free in solution (note that the channel cross-section does not need to be square). The exact shape and/or dimensions of the nanochannel are not crucial for the stretching.

In a final aspect the invention relates to the use of the nanochannel device for the mapping of the local AT/GC ratio along the DNA.

DETAILED DESCRIPTION OF THE INVENTION

Figure 1:
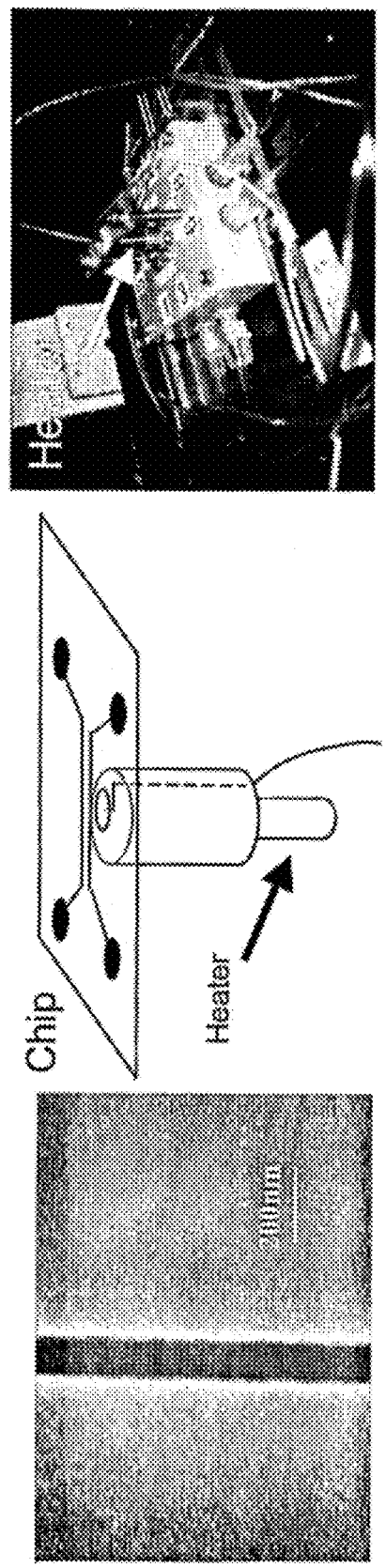
FIG. 1. (LEFT) shows a detailed image of a nanochannel. (CENTER) Temperature control directly through a heating element with an integrated thermoelement. (RIGHT) Chip mounted in heating complex on an inverted microscope equipped with an EMCCD camera. Tubing for pressure control of the movement of the DNA.

The invention relates to a simple and effective method for the mapping of the local AT/GC ratio along the DNA in which the DNA is denaturated either by heat or by chemical treatment to partially melt a double-stranded DNA molecule, i.e. to partially transform the double-stranded DNA into single-stranded (denaturation). In this way the map of the local AT/GC ratio along the DNA is made visible. The probability of denaturating/melting is directly related to the ratio of AT to GC at scales >500 bases. On a shorter length scale cooperative effects are important and the relationship is not as simple. However, the theory for melting is well-established and is based on work by Poland and Sheraga in the 1960s [D. Poland and H. A. Scheraga, "*Occurrence of a phase transition in nucleic acid models*", J. Chem. Phys. 45: 1464-1469 (1966).]. The method includes the steps of staining DNA with fluorescent dye, the emission of which is sensitive to whether the DNA is ssDNA or dsDNA, introducing the DNA into a device and if necessary stretch the DNA and denature the DNA and observing the resulting pattern of the DNA. By the invented method it will for the first time be possible to analyse long pieces of DNA as long as the DNA can be stretched out. The denaturation may be performed by the use of a heating source, which increases the heat from about 18° C. to about 99° C.

As an alternative or complement to the heating, the melting of the DNA can be implemented by changing the buffer conditions so that the DNA is more prone to denaturation, for example by the addition of formamide.

There is little need of sequence alignments and no need to use probes or restriction enzymes, although sequence specific probes (and/or restriction enzymes) can be combined with our technique to create landmarks along the DNA. Within a typical field of view, using a meandering channel, at least 100 µm×100 µm of DNA can be analysed corresponding to roughly 30 Mbp. If needed the resulting pattern due to the denaturation/melting can in itself be used to align different smaller pieces of DNA, in order to obtain a melting map of a larger DNA sequence from fragmented DNA molecules. The technique can easily be integrated within a lab on a chip system enabling single-cell measurements.

In another embodiment the invention relates to a method for the mapping of the local AT/GC ratio along DNA comprising the steps of providing DNA having a length of about 1 kbp or more, staining said DNA with a fluorescent dye, changing the buffer conditions and obtaining a pattern showing the distribution of the nucleotides. The DNA may be stretched prior to that the buffer conditions are changed. The stretching may be performed in a device such as a nanochannel device.

The local melting is a function of the local AT/GC ratio (i.e. the ratio of the number of AT basepairs and the number of GC basepairs within a small window of for example a few hundred basepairs along the DNA; current standard imaging technologies limit the window size to roughly a thousand basepairs) so that the observed change in fluorescence along the DNA can be used to assess the local AT/GC ratio along the DNA. The change in fluorescence can be due to change in the optical properties of the dye or the binding properties of the dye as a function of whether the DNA is double stranded or single stranded: the quantum yield may increase or decrease when the DNA melts, the absorption and/or emission spectra may shift, the dye may bind in a different mode, the dye may simply unbind or bind specifically when the DNA melts by an increase in temperature or increase in concentration of denaturant (such as formamide or urea). During the denaturation/melting the DNA starts to unfold and different features along the DNA are visible at different temperatures. For example, the detailed structure of AT-rich areas is accessible at low temperatures and is completely obscured at higher temperatures when the whole region is fully melted. On the other hand, AT-poor regions will not show any detailed structure until the temperature reaches a relatively high level. Thus to access information about the local AT/GC ratio for a large dynamic range of local AT/GC ratios, data is acquired for an entire range of temperatures (or denaturing conditions, such as formamide concentrations).

In a first step the DNA to be analysed needs to be purified so that the histones are removed as well as other proteins. Purification may be done by any suitable method well-known for a person skilled in the art. For example, any method disclosed in the well-known manuals Sambrook et al. ("*Molecular Cloning.: A Laboratory Manual*", Cold Spring Harbor Laboratory Press, Cold Spring Harbor, N.Y., 1987) and Ausubel et al. ("*Current Protocols in Molecular Biology*", Greene Publishing Co., 1995) may be used.

In a second step the DNA will be stained with a fluorescent dye, such as an intercalating dye. The dye to be used must interact differently with ssDNA and dsDNA such that differences can be detected by optical methods. There are several dyes which may stain DNA and a person skilled in the art can use any suitable stain as long as the dye binds to the DNA and changes properties upon (local) melting of the DNA. The dye may be such that it binds differently to ssDNA and dsDNA or that it has different optical properties for ssDNA and dsDNA. One example of a group of dyes is homodimeric, monomethine cyanine dyes where there is a large shift in emission and/or excitation wavelength between dsDNA and ssDNA, [Timtcheva, L, et al., "*Homodimeric monomethine cyanine dyes as fluorescent probes of biopolymers*". Journal of Photochemistry and Photobiology B-Biology, 2000. 58(2-3): p. 130-135.].

Another example of dyes include different cyanine dyes, which may be obtained from Invitrogen (www.invitrogen.com) such as TOTO-1™ and YOYO-1™ (1,1'-(4,4,8,8,-tetramethyl-4,8-diazaundecamethylene)bis[4-[[3-methylbenzo-1,3-oxazol-2-yl]methylidene]-1,4-dihydroquinolinium] tetraiodide). More examples from Invitrogen include POPO-1™, BOBO-1™, JOJO-1™, POPO-3™, LOLO-1™, BOBO-3™, YOYO-3™ and TOTO-3™.

Another alternative is to use a molecule that binds specifically to ssDNA and that can be fluorescently stained or is fluorescent in itself. One such example is single-strand binding protein (SSBP).

Examples of changes that can be detected upon local melting of the DNA: emission is switched on or off, emission intensity is changed, emission and/or excitation spectra are shifted, fluorescence life-times are changed, polarization anisotropy is changed.

The ratio between the lit up and the dark areas gives a measure of the local melting and thereby the local AT/GC ratio. It is necessary to take into account the local density of contour as well as the fluorescence intensity as a function of whether the DNA is single stranded or double stranded.

Depending on the DNA to be analysed different buffers may be used. A person skilled in the art may easily find out which buffer to use for different analyses and if there is a need to decrease the melting temperature several options are open, for example: addition of formamide (competes with the hydrogen bonding between the bases), working at low salt conditions (decreased screening of the repulsive electrostatic interaction between the ionized phosphate backbone) or addition of urea. An optimization of the buffer conditions takes into account not only the effect on the melting of the DNA, but also effects on the performance of the dye molecules used. To avoid photobleaching it is important to add mercaptoethanol or dithiothreiotol (DTT) and an oxygen scavenger system (for example: glucose, catalase and glucose oxidase) to the buffer. Several methods as well as buffers are disclosed in the well-known manuals Sambrook et al. ("*Molecular Cloning: A Laboratory*

Manual", Cold Spring Harbor Laboratory Press, Cold Spring Harbor, N.Y., 1987) and Ausubel et al. ("*Current Protocols in Molecular Biology*", Greene Publishing Co., 1995) may be used.

Prior to being analysed the DNA may be stretched to gain optical access to the entire DNA. Free DNA in solution is arranged in a random coil, where any detailed information along the DNA is blurred by the overlap of different segments of the DNA molecule. The relevant measure of resolution is not in units of length but in units of nucleotides. Confinement of DNA in nanochannels is one approach to stretching DNA that can readily be integrated within a Lab on a Chip [Tegenfeldt, J. O., et al., "*The dynamics of genomic-length DNA molecules in* 100-*nm channels*". Proceedings of the National Academy of Sciences of the United States of America, 2004. 101(30): p. 10979-10983.]. Here smaller channels and/or lower ionic strengths in the buffers give better stretching, which in turn give better resolution in the measurements of the dyes attached along the DNA. In addition to confinement in nanochannels, there are several alternative methods that may be used.

In one approach stretching of the DNA may be to use a shear flow in a micro fluidic channel. The difference in velocity in different locations in the microfluidic device will simply impose different forces at different parts of the DNA leading to a net tension and thus a stretching of the DNA. Funnel-like structures as well as crossed channels can be used.

Another approach may be to tether the DNA in one end to the substrate and allow the flow of buffer to stretch the DNA. This can be done by functionalizing one end of the DNA with for example a thiol so that it sticks to a gold line on a surface. It can also be implemented by allowing a drop of DNA solution to fall over a surface which has been treated with positively charged groups such as amino groups [Cai, W. W., et al., "*Ordered Restriction-Endonuclease Maps of Yeast Artificial Chromosomes Created by Optical Mapping on Surfaces*". Proceedings of the National Academy of Sciences of the United States of America, 1995. 92(11): p. 5164-5168.].

In a third approach, a structure with a two-dimensional confinement with integrated pits may be used. The DNA will be attracted to the pits to gain entropy, and a long DNA can thus be attached between two pits in a stretched conformation.

Other approaches may include optical and/or magnetic tweezers. When the DNA has been stretched and stained with a dye, such as an intercalating fluorescent dye, there will at least be a step of denaturating said DNA, which may be done either chemically or by a temperature step in which the DNA is exposed to an increased temperature. The practical temperature range is determined by the limits imposed by the optics of the microscope, primarily the temperature range of the microscope objective. Typically, the temperatures involved can be decreased by using an appropriate buffer composition. One example being that the DNA is exposed to an increased temperature range from about 18° C. to about 99° C., such as for example 30-70° C., 30-50° C., 30-40° C., 40-50° C., 40-60° C., 40-70° C. With a ramp of temperatures, the actual AT map is constructed by a combination of the maps at the individual temperatures. At low temperatures, regions rich in AT are mapped out in detail and at high temperatures, regions rich in GC are mapped out. The results can be seen as a set of data each set acquired with a limited dynamic range in terms of AT concentrations. In practice a gray scale image is constructed with one axis representing the length of the DNA, one axis representing the temperature and the gray scale of each pixel represents the degree of local melting. The entire gray scale thus represents the lowest to the highest local AT/GC ratios.

An alternative approach to the temperature ramp as described above is to gradually change the buffer conditions while keeping the temperature constant. For example, keep the temperature at 35° C. and gradually increase the formamide concentration from 0% to 50% or even up to 70% or more to enable operation at even lower temperatures. After each temperature step (or increase in concentration of denaturant such as formamide) the AT/GC ratio along the DNA is detected. Primary means of detection of AT rich segments is optical measurement of fluorescence of dyes bound along the DNA. The detected fluorescence may change in a number of ways as a function of AT/GC ratio: emission is switched on or off, emission intensity is changed, emission and/or excitation spectra are shifted, fluorescence life-times are changed, polarization anisotropy is changed.

The basic tool is diffraction limited standard fluorescence microscopy, but to go beyond the 200 nm resolution of a typical fluorescence microscope operated at visible wavelengths and using good objectives, various recently developed super resolution microscopes may be used instead, such as stimulated emission depletion (STED) microscopy, stochastic optical reconstruction microscopy (STORM) and fluorescence imaging with one nanometer accuracy (FIONA, SHREK) providing at least an order of magnitude improvement in resolution over the standard diffraction limited fluorescence microscope. Another alternative may be the use of on-chip imaging, fluidics channels integrated with nanoscale apertures, negative index of refraction devices, local enhancement using gold nano structure (essentially aperture less SNOM), Shah-transform-based approaches [Zenhausern, F. and C. Chia-Fu, "Near-field transform spectroscopy", U.S.P. Office, Editor. 2005, Motorola Inc.: USA.] or other optofluidics microscope [Heng, X., et al., "*Optofluidic microscopy—a method for implementing a high resolution optical microscope on a chip*". Lab on a Chip, 2006. 6(10): p. 1274-1276.].

Furthermore, the method may include a final step, which includes image analysis and data processing using a computer aided system.

The invented method may be used for a number of DNA analyses including but not limited to mapping of structural variations (deletions, insertions, inversions, translocations, CNV), haplotyping, analyzing highly repeated sequences, pathogen detection and identification, water quality control, food quality control, forensics, personalized medicine, gene mapping for diagnostics and sequence alignment for sequencing purposes. Another example is single-cell gene mapping for measurement of variation between individual cells as well as measurements on rare cells. The invented method can find use both in basic and applied research as well as in clinical work complementing existing cytogenetics and genomics techniques. Another approach may be to use the method for heteroduplex analysis. Sample DNA is hybridized to a reference DNA. Using melting mapping the goodness of the match between the sample DNA and the reference DNA can be measured. Any mismatch in the dsDNA would decrease the local melting temperature at the location of the mismatch resulting in a melted region for the mutated DNA strand hybridized to a (normal) reference DNA strand and an absence of a melted region for two normal DNA at a given selected temperature. A similar approach may be used for methylation mapping by comparing the melting maps of duplexes created by hybridization of untreated sample DNA with reference DNA and by hybridization of bisulfite treated sample DNA with reference DNA. The bisulfite method replaces any methylated cytosine with an uracil and therefore changes the sequence of the DNA. This in turn changes the melting profile of the DNA [Borresen, A. L., et al., "*Constant denaturant gel-electrophoresis as a rapid screening technique for P53 mutations*". Proceedings of the National Academy of Sciences of the United States of America, 1991. 88(19): p. 8405-8409.].

The invention also relates to a nanochannel device comprising at least one nanochannel having a first inlet and a second outlet and a heating source for heating said nanochannel.

The nanochannel device may be made of silica, silicon or plastic material. The nanochannel device may have one nanoslit perpendicular to said nanochannel. In one embodiment the nanochannel device has a nanogroove structure adjoining the nanochannel and the nanoslit and optionally the device may have an array of nanochannels having one nanoslit perpendicular to said nanochannels and an array of nanogrooves adjoining the nanoslit and nanochannels. In another embodiment the nanochannel device may have heating sources for heating said array of nanochannels having one nanoslit perpendicular to said nanochannels and an array of nanogrooves adjoining the nanoslit and nanochannels. Example of a nanochannel device is shown in the figures.

In an alternative embodiment the invention also relates to a nanochannel device comprising at least one channel having a length from 10 microns to several hundreds of microns or even longer and with a channel cross-section that is 30 nm×30 nm up to 900 nm×900 nm or even larger provided the channel cross section is smaller than the size of the DNA free in solution. Other examples include a nanochannel device having from 1 to several hundreds of channels, such as 1-1000 or 1-100. Additionally, the channel section may have a cross section from 30 nm×30 nm up to 600 nm×600 nm or 30 nm×30 nm up to 300 nm×300 nm. Said nanochannel device may be made of silica, silicon, plastic material or any other suitable material.

The nanochannel may be straight for relatively small DNA or meander shaped to accommodate a single large DNA within one field of view.

To facilitate the fluidics, the nanochannel or nanochannels are connected to two larger channels on the micrometer scale, typically 1-10 microns deep and 50 microns wide. The larger channels are connected to two reservoirs each such that in a first step the sample is driven to a close proximity of the nanochannel and then in a second step driven directly into the nanochannel. The sample can be driven by a pressure difference between two reservoirs or by an electrical field.

Figure 6:
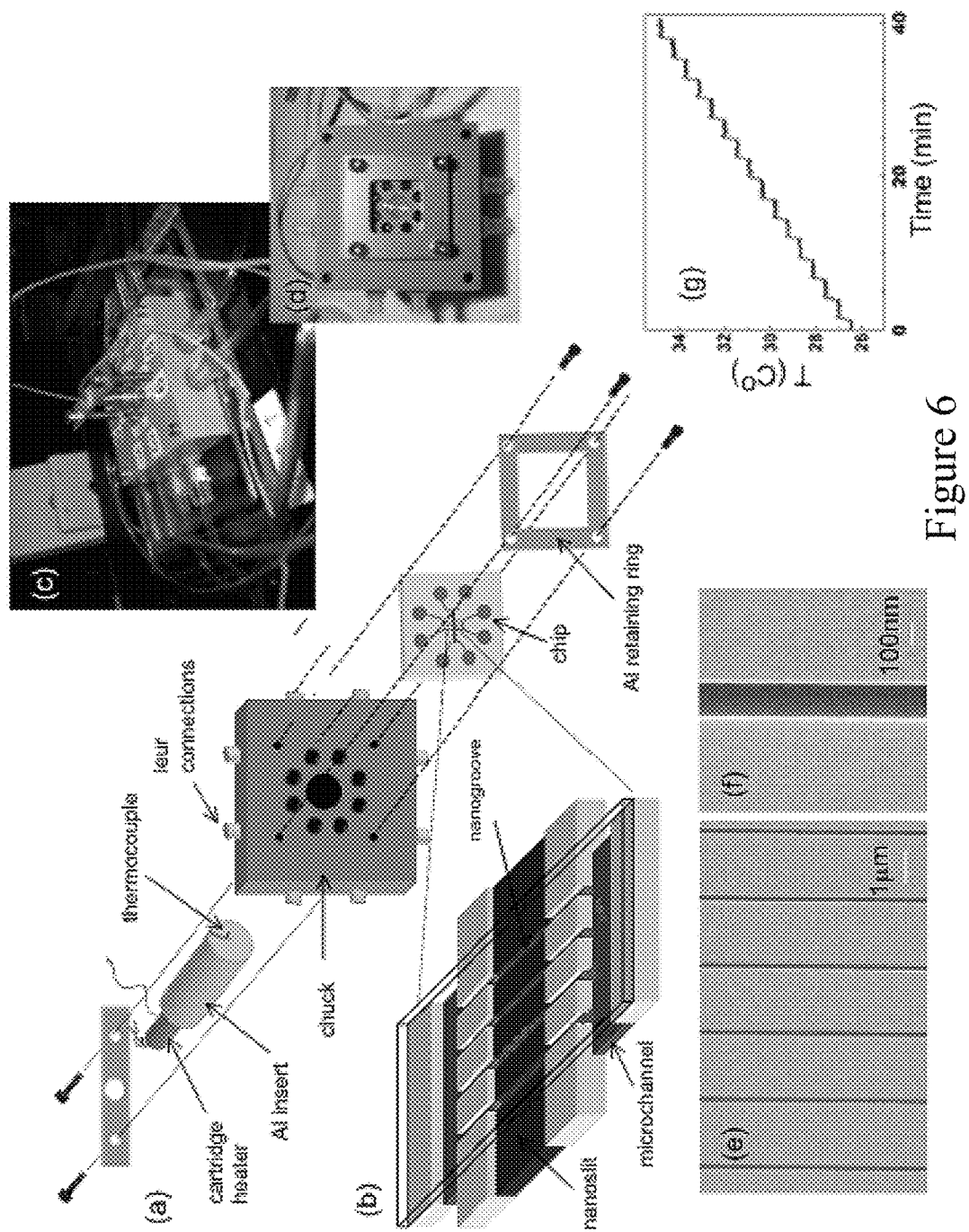
FIG. 6 shows a) A schematic showing how the chip, fluidic chuck and heater are assembled and integrated in an experiment, (b) A 3D-diagram of the nanogroove and nanochannel arrays with microloading channels. Cartoon DNA molecules are shown in red. (c) Photograph of the chuck-chip-heater assembly on the microscope stage with external tubing for applying pressure, (d) Photograph of a chip clamped to the chuck via the Al retaining ring, (e) Low magnification SEM micrograph of the nanochannels (f) high magnification SEM micrograph of a nanochannel (150 nm wide 120 nm deep), (g) Temperature read-out from backside thermocouple during a thermal ramp. Images were acquired at each step in the cycle.

The nanochannels can be combined with a nanoslit forming a nanogroove structure to facilitate the loading of the DNA (see FIG. 6). The nanogroove structure comprises nanochannels with a small gap between the substrate and the sealing. The small gap extends into channels that in turn are connected to reservoirs. This allows fluid or DNA to be driven to or from the sides. By driving the DNA into the grooves with a driving force that goes into the nanogrooves but out to the sides, the DNA can be collected and concentrated in the nanogroove structure. The nanoslit structure also allows for the continuous changing of buffer conditions around the stretched DNA. The DNA is first trapped in the nanogrooves. The buffer is then flown perpendicularly over the DNA from one side of the device to the other inside the nanoslit.

In one embodiment the DNA is stretched in a chip made in for example fused silica. The chip is mounted in a chuck that can be mounted in a fluorescence microscope. The chuck contains a heating element and a device to measure the temperature locally at the chip. In addition, the chuck contains holes drilled and threaded for connection to fluidics systems, electrodes for electrokinetic drive, vacuum pump and/or pressure control units. The fluorescence microscope uses a light-sensitive camera (see FIG. 6).

Heating can also be realized by local heating using an absorptive coating within or in close proximity to the nanochannels in the device combined with illumination of selected parts of the device.

Local heating can also be realized by absorptive particles or molecules in the buffer solution combined with illumination of selected parts of the device.

Another alternative is to pass a relatively large electric current through the device to induce sufficient Joule heating to raise the temperature to the desired level.

EXAMPLE

Example 1

The device is made in fused silica using standard electron-beam lithography combined with UV-lithography and reactive ion etching. It is placed in a dedicated chuck for temperature control and mounted on an epifluorescence microscope (FIG. 1). Lambda-phage DNA is dyed with a conventional intercalating dye (YOYO-1™ Invitrogen) and dissolved in a buffer with low ionic strength (0.05 TBE+ 10 mM NaCl) and 33% and 50% formamide respectively to decrease the melting temperature.

Results

Uniform fluorescence is seen along each DNA molecule at room-temperature, and with rising temperature, dark patches appear along the DNA corresponding to AT-rich regions that lose in intensity due to local melting of the double-stranded helix thereby resulting in a "barcode" pattern along the DNA. The asymmetric pattern is consistent across all molecules viewed (FIG. 2) and corresponds to AT-rich regions in the middle and on one side of lambda-phage DNA (FIG. 3).

Figure 7:
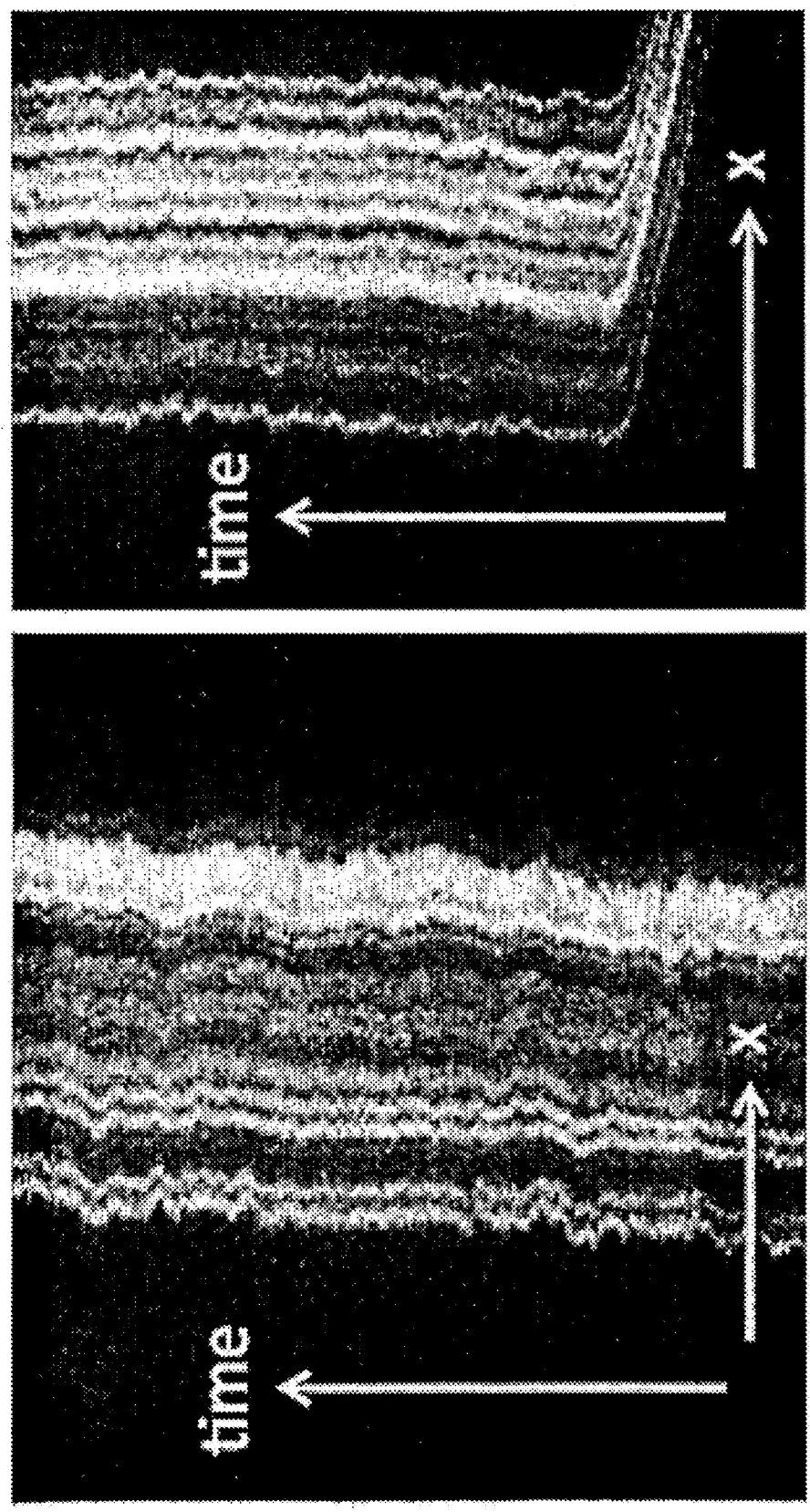
FIG. 7 shows fluorescence kymograph traces demonstrating melting of two human female DNA fragments (200 kbp each) in solutions of 0.05×TBE+ 10 mM NaCl with 50% formamide (by volume) acquired at 28° C. The x-axis is along the length of the DNA.

Gradually increasing the temperature reveals different details along the DNA. Working at 33% formamide (FIG. 4) and 50% formamide (FIG. 5) gives the same information, but at a more than 100 C lower temperature for the higher formamide concentration. Another example is two human female DNA fragments (each approximately 200 kbp) are melted at 28° C. (see FIG. 7).

Example 2

Fabrication

Figure 8:
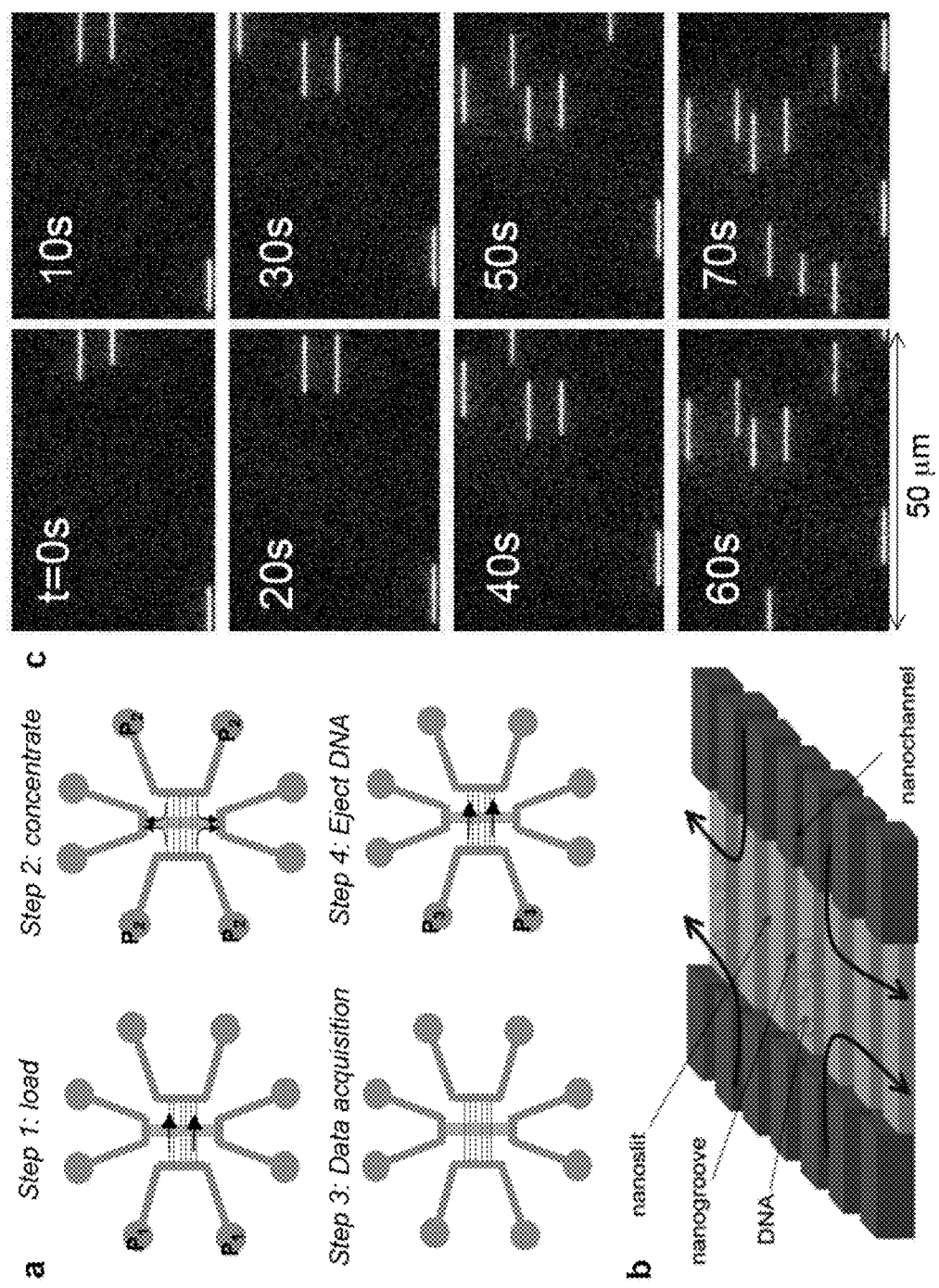
FIG. 8: shows a Device Loading Protocol (a) Molecules are loaded (1) with pressure Pi ~2 bar and resulting in a velocity of the DNA of vDNA ~250 µm/s; then concentrated (2) with P2—0.3 bar (VQNA ~5 µm/s), imaged (3) in equilibrium and ejected (4) with P3—I bar. (b) Three-dimensional schematic of the circulating flow pattern (purple arrows) created by applying equally distributed pressure to the four reservoirs adjoining the nanochannel array. The effect of this flow is to symmetrically drive molecules from the nanochannels into the nanogrooves where they will remain trapped by the entropic barrier between the nanogrooves and nanoslit. (c) Time-series of λ-DNA being concentrated in nanogrooves
Figure 9:
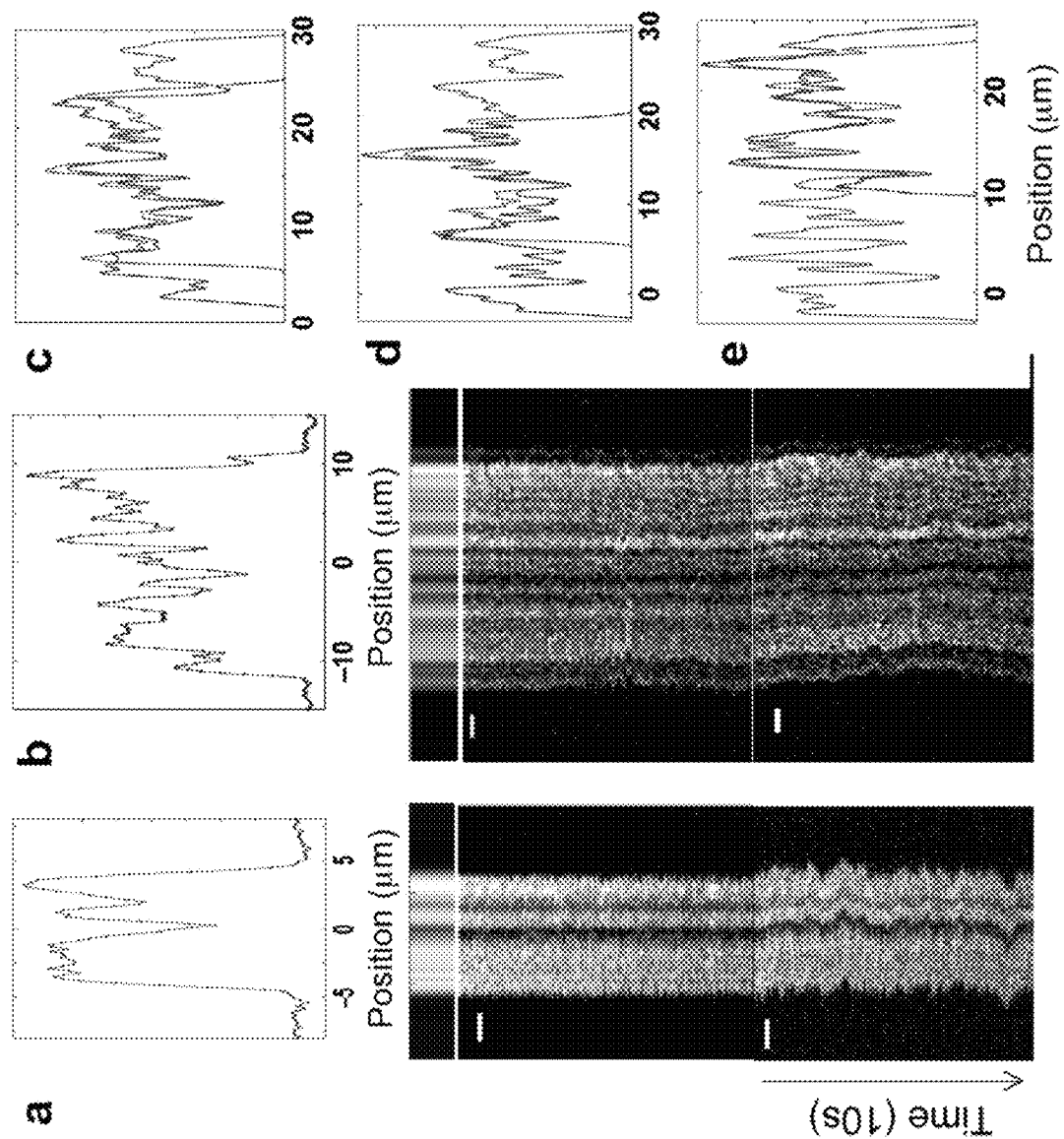
FIG. 9 shows time-trace rescaling and correlation analysis, (a) An example of the rescaling procedure for λ-phage DNA. (Bottom) Raw time-trace of molecule (integrated intensity transverse to channel for each recorded frame). (Middle) Rescaled time-trace. (Top) Intensity profile obtained by averaging over rescaled frames. Barcode shown below plot is graphed data displayed as a grayscale plot, (b) Rescaling procedure for example BAC RPl 1-125C7 molecule, (c, d) Examples of RPl 1125C7 molecule aligned by correlation to template of same sequence, (e) Raw T4GT7 fragment aligned by correlation. The scale bar in all images is 2 µm.
Figure 10:
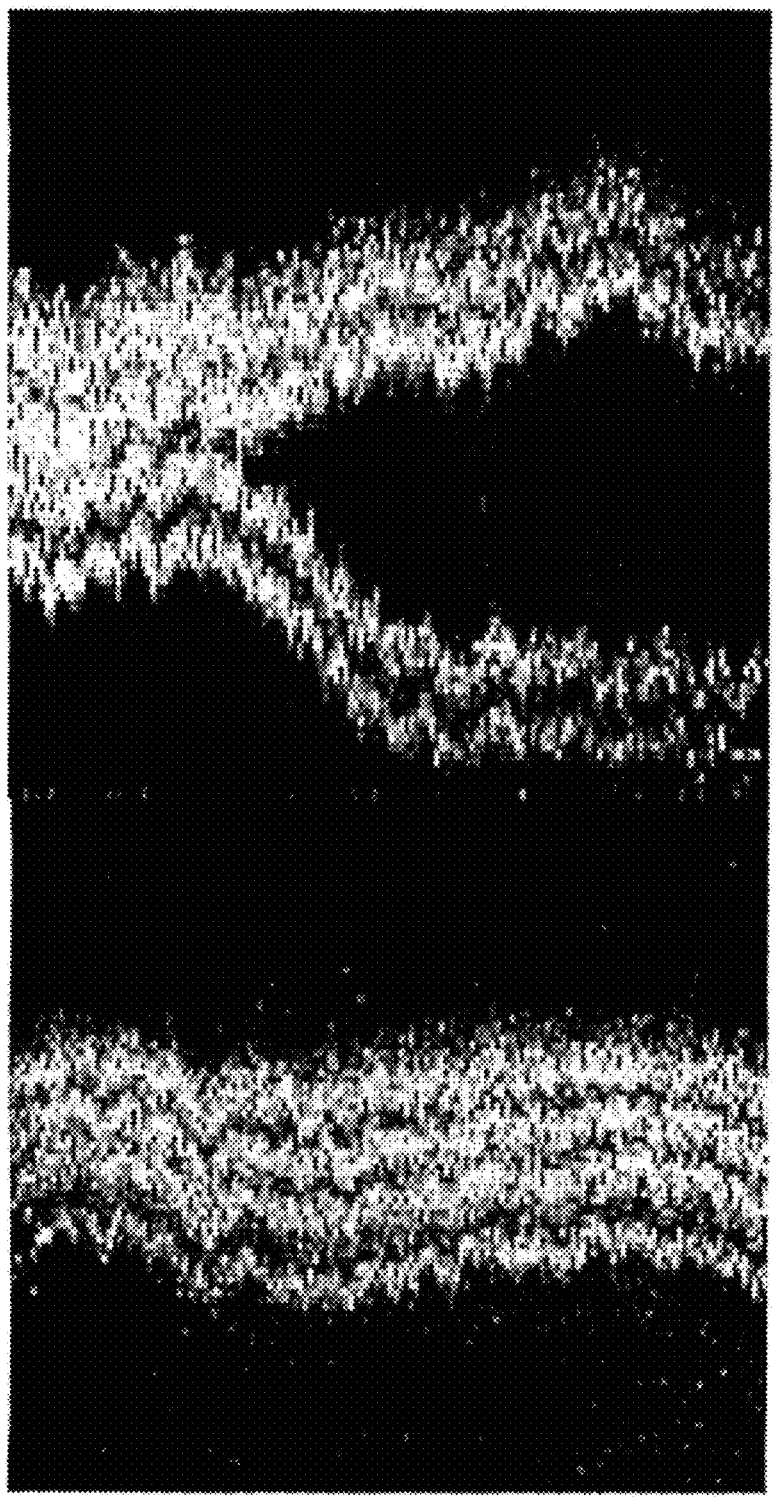
FIG. 10 shows an example of a time trace of partially denatured T7 DNA. The timetrace allows the user to distinguish between dark regions due to denaturation and dark regions due to breakage of the DNA.
Figure 11:
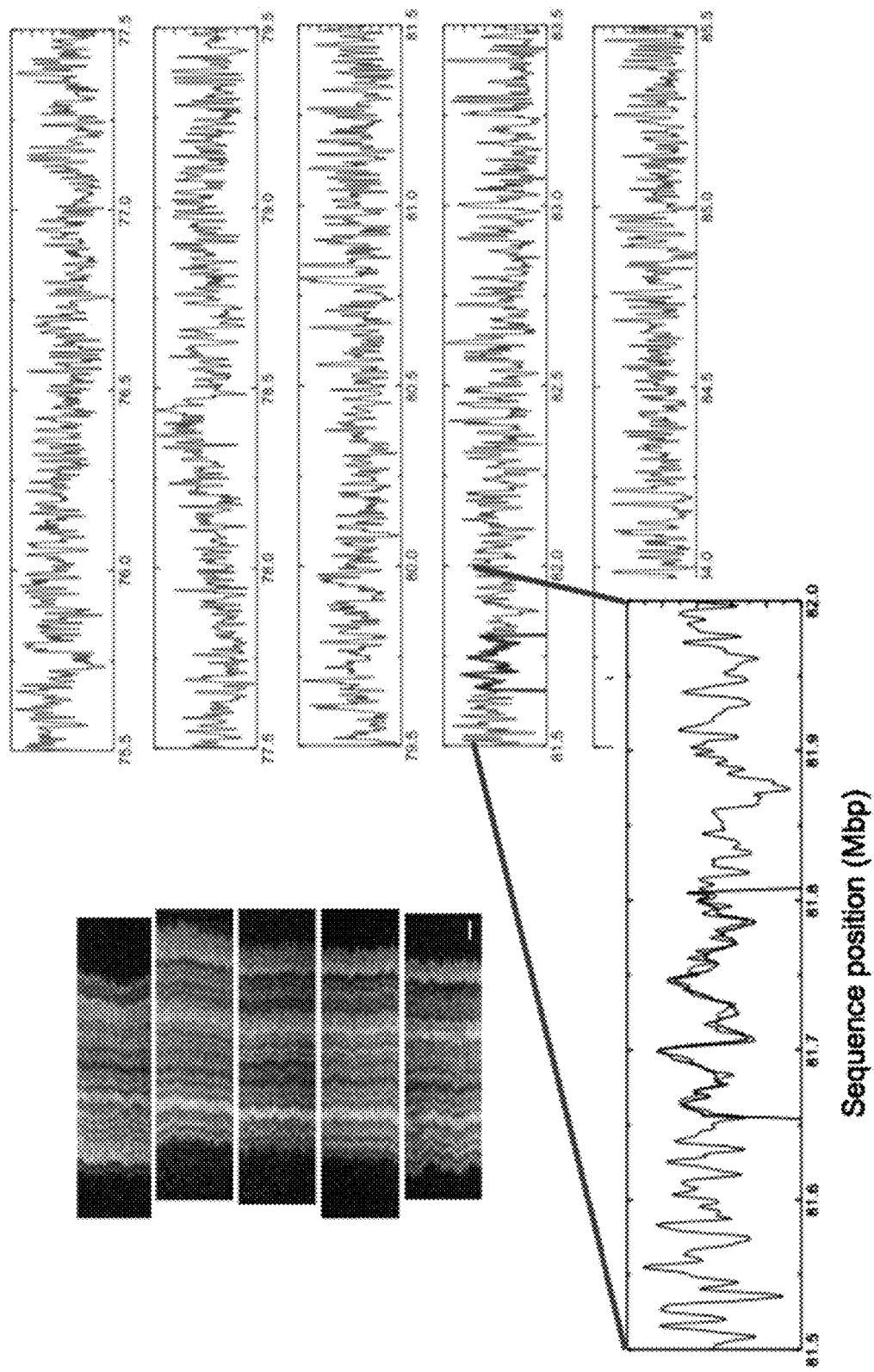
FIG. 11 shows (upper left) Barcode raw data for BACRP11-125C7 arranged to emphasize barcode overlap. Data acquired with 48% formamide at 27° C. The scale bar is 2 µm. (lower left and right) Alignment of RP11-125C7 to 10 Mbp of sequence from chromosome 12. The melting profile of the human genome calculated between position 75,500,000 and 85,500,000 of chromosome 12 with aligned RP11-125C7 (blue). Profile calculated at 59° C. for 5 mM NaCl (corresponding to an estimated melting temperature of 29° C. in 48% formamide). (lower left) Selected 500 kbp of melting profile around the position of RP11-125C7.
Figure 12:
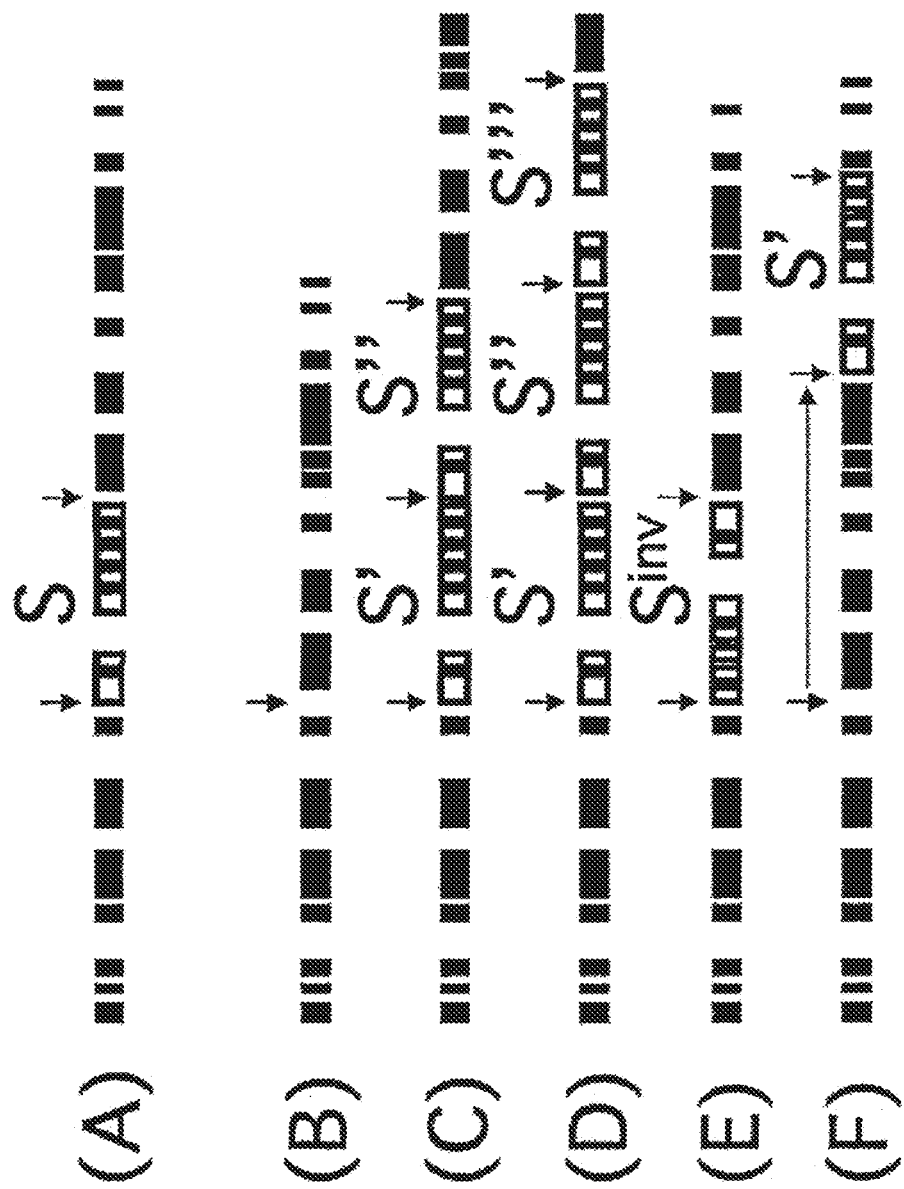
FIG. 12 shows the basic illustration of the idea of using the pattern along the DNA as a barcode for identification of locations along the DNA and their structural variations. The rows correspond to the barcodes of different DNA molecules. (A) is the reference barcode, either measured or calculated based on known sequence and known melting theory. (B) is an example of a deletion, where the region S in the reference DNA is removed. (C) is an example of a duplication where the region S in the reference DNA occurs twice, S' and S". (D) is an example of a triplication where the region S in the reference DNA occurs three times, S1, S" and S'". (E) is an example of an inversion, where the sequence of the region S in the reference DNA is inverted. (F) is an example of a translocation of the region S in the reference DNA to another location, S'.
Figure 13:
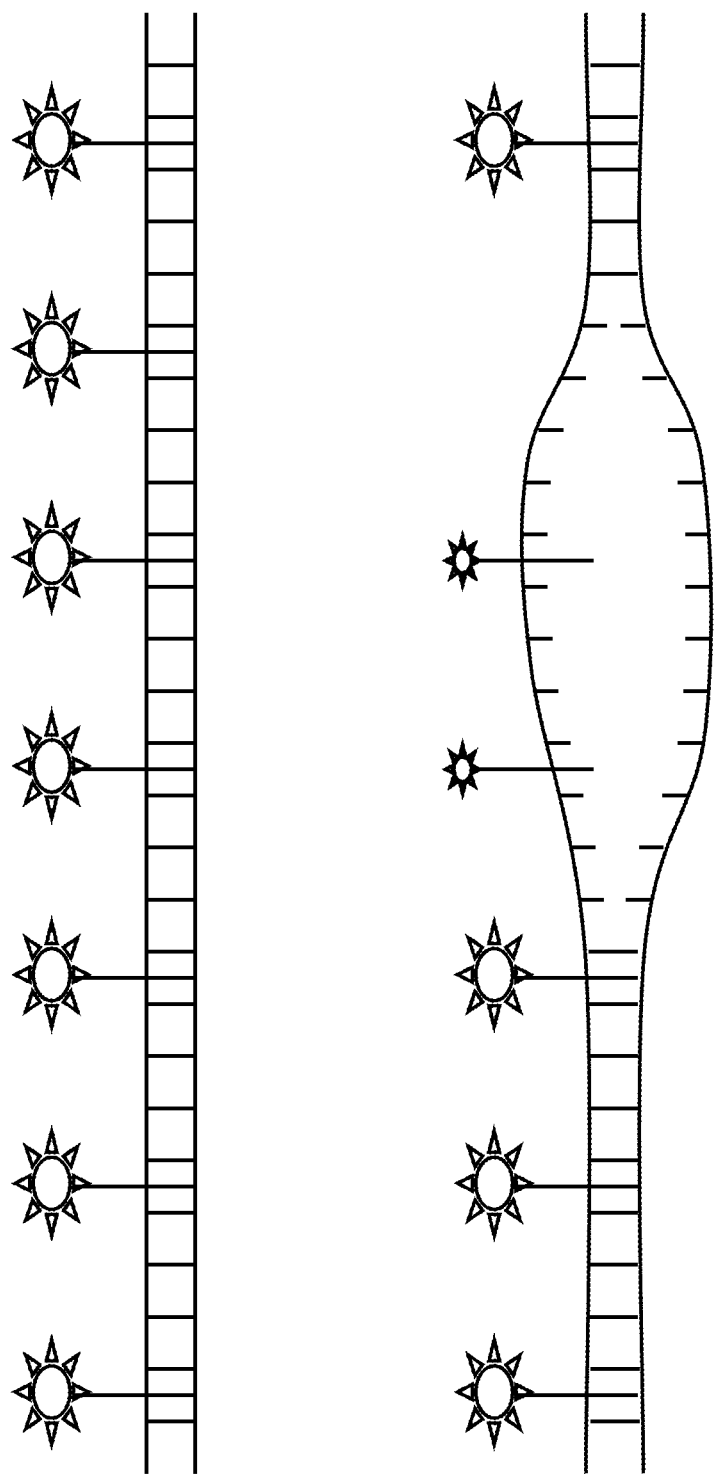
FIG. 13 shows the basic idea of staining the DNA for melting mapping. Dyes emit and bind differently for double-stranded and single-stranded DNA.
Figure 14:
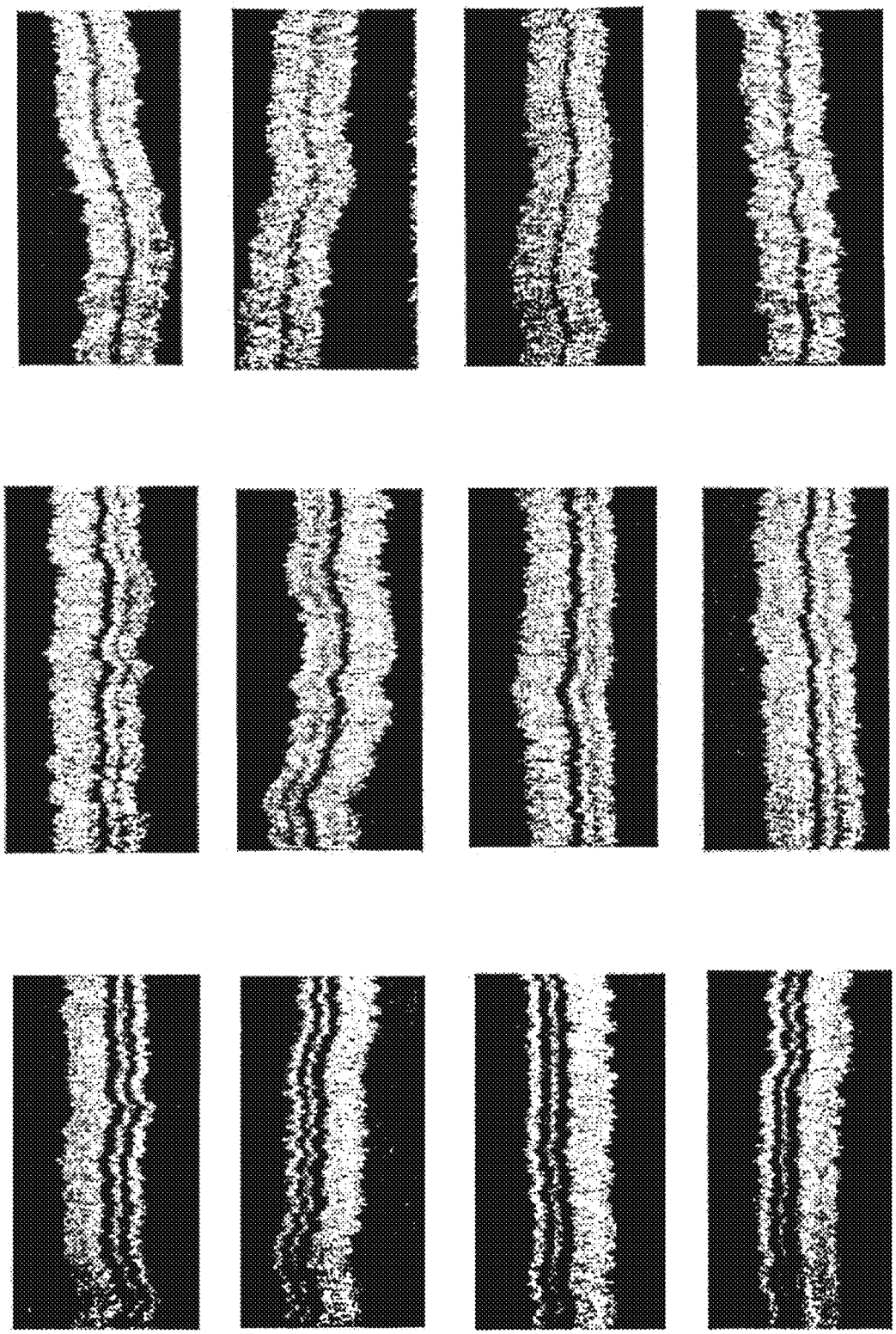
FIG. 14 shows twelve different lambda phage DNA molecules in 1 mM NaC, 0.05×TBE, 50% formamide. Each time trace is 20 sec. Width of each image is 16.4 µm. Temperatures are for top row: 29.2° C., middle row: 30.50 C and bottom row: 32° C.
Figure 15:
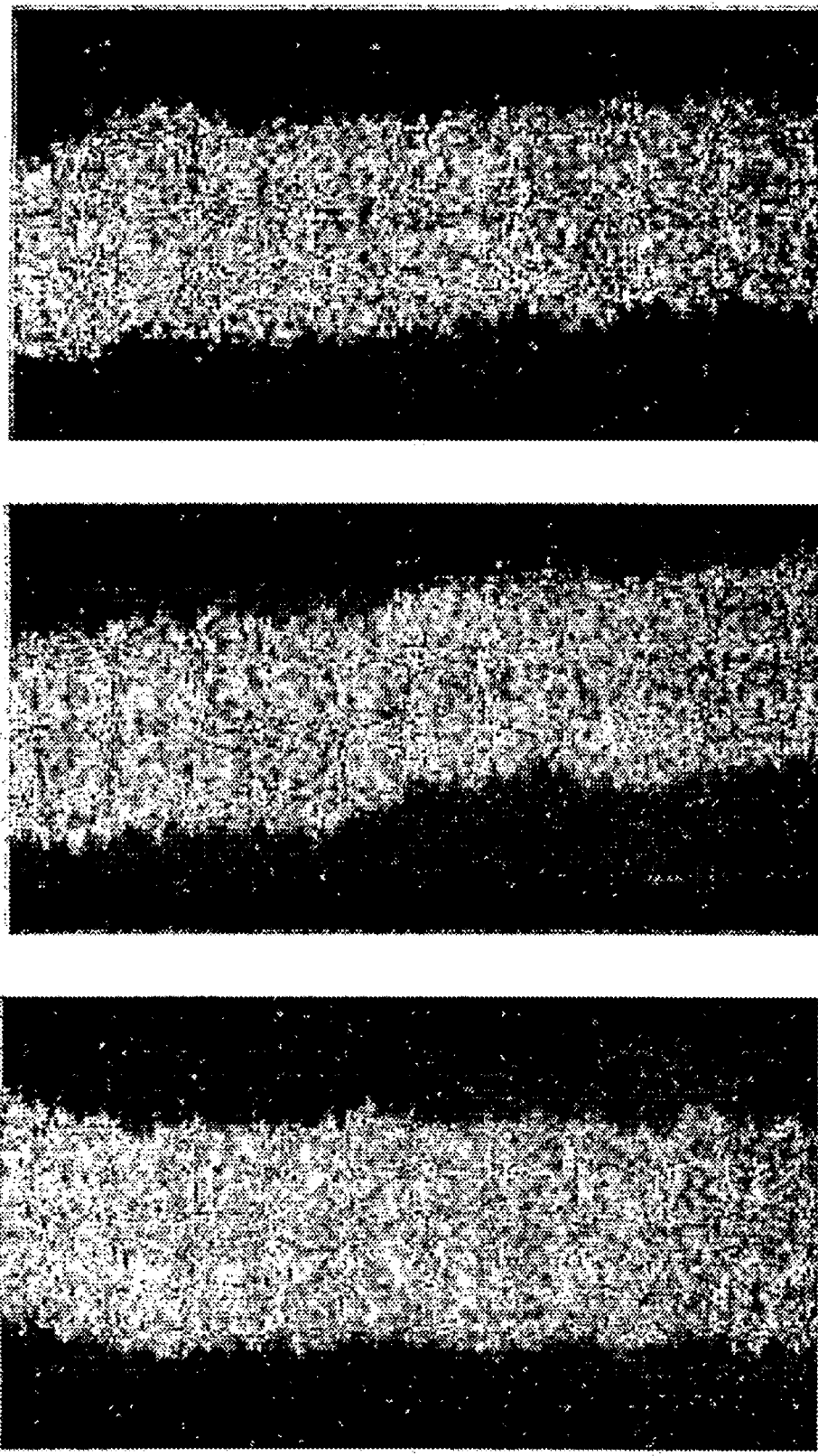
FIG. 15 shows three different lambda phage DNA molecules in 10 mM NaC, 0.05×TBE, 50% formamide. Each time trace is 20 sec. Width of each image is 16.4 µm. Temperature is 23° C.
Figure 16:
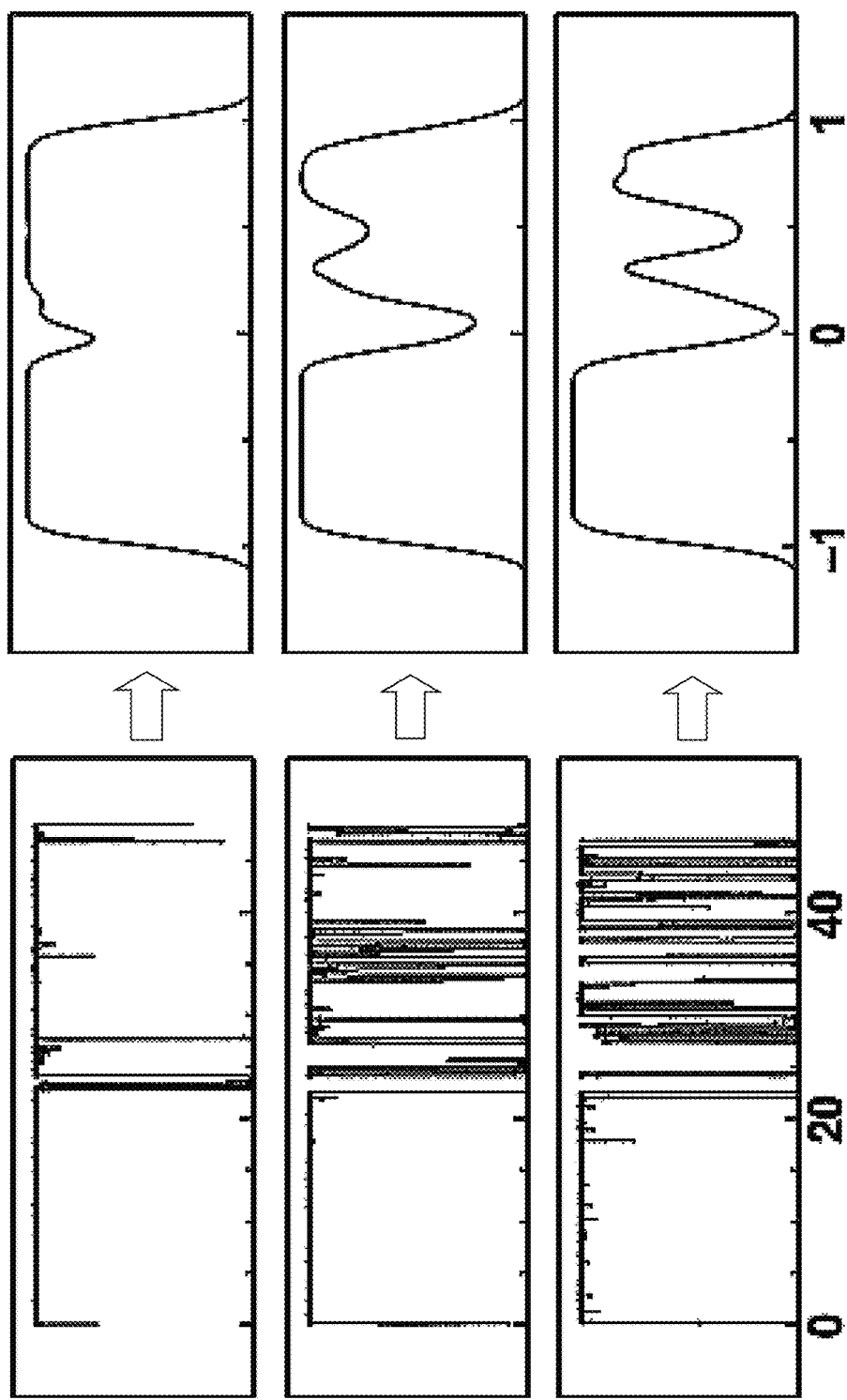
FIG. 16 shows the theoretical melting curves for lambda-phage DNA for temperatures 42.15° C., 45.81° C., 48.69° C. (top to bottom). The left curves are helicities (probabilities that the DNA is double-stranded) as a function of location along the lambda-phage DNA molecule. The right curve is a convolution of the respective helicity curve with the point-spread function of the optical system, here approximated with a Gaussian with standard deviation 200 nm.
Figure 17:
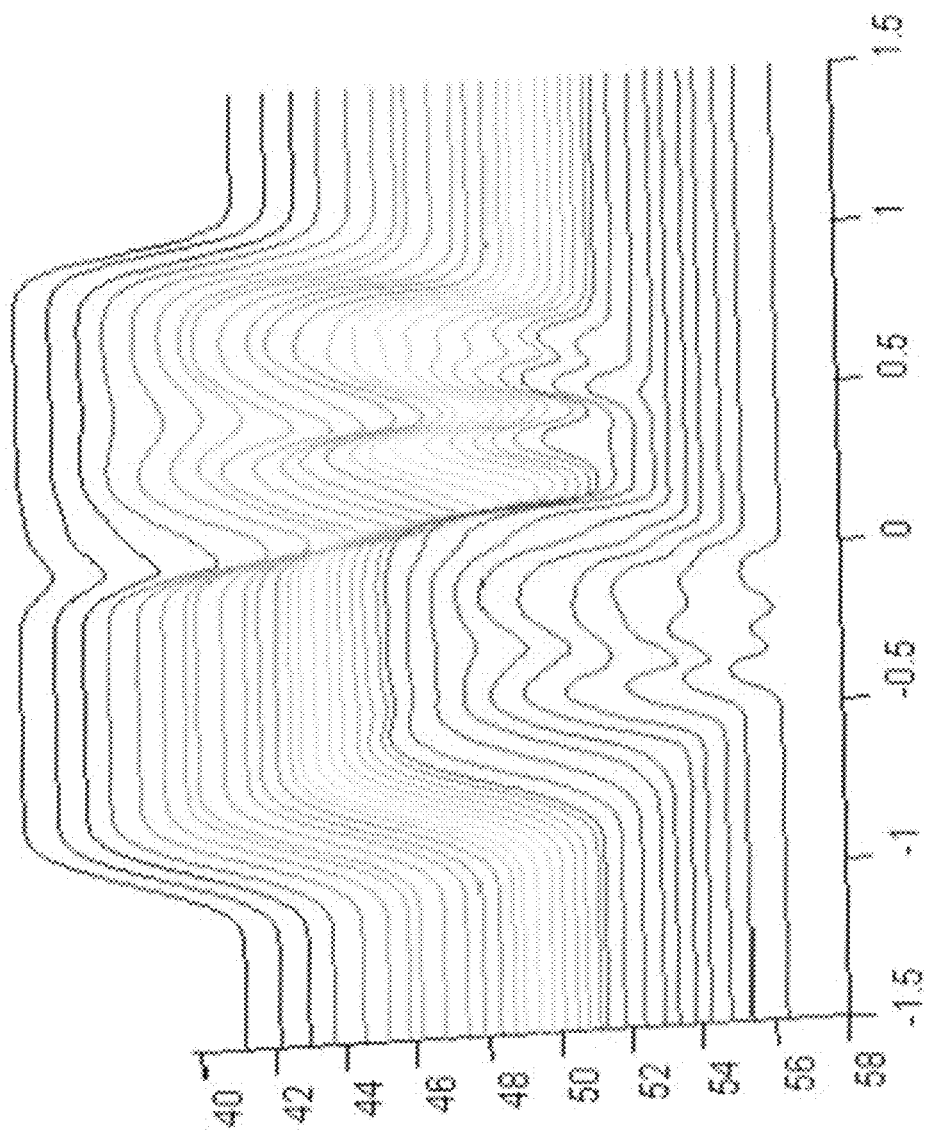
FIG. 17 shows the theoretical melting curves for lambda-phage DNA for a range of temperatures in the interval 40° C. to 58° C. The left axis represents the temperature in ° C. and the bottom axis represent the fractional length of the DNA molecule; −1 to 1 correspond to the full length of the molecule without any denatured regions.

The devices were fabricated on fused silica wafers (HOYA) via a three stage process combining electron beam and UV contact lithography. A 200 µm long array of 120-150 nm wide nanochannels spaced 2 µm apart was defined using electron beam lithography (JEOL) in zep520A resist and then transferred to the silica substrate via CF4:CHF3 reactive ion etching (RIE). Contact UV lithography was then used to expose a 350 µm long and 50 µm wide nanoslit in photoresist running perpendicular to the nanochannel array. The slit was etched using RIE to a depth of 30 nm. Where the slit and the nanochannel array intersected, an array of nanogroove structures was formed; see FIG. 8. In order to introduce buffer into the nanoslit and nanochannels, a last UV contact lithography and etching step was used to define a 50 µm wide microchannel 1 µm deep in U-shaped arms adjoining the nanoslit and nanochannels (FIG. 8). Loading holes were sandblasted in the reservoirs (eight total) and the chip was sealed using direct silica-silica bonding to 150 µm thick fused silica coverglass (Valley Design) so that high numerical aperture oil immersion objectives could be used. Etch depths were measured using a profilometer.

The experiments were performed with λ-phage DNA (48.5 kbp, L=16.5 µm, New England BioLabs), T4GT7 DNA (166 kbp, L=56.4 µm, Nippongene), T7 DNA (39.9 kbp, L=13.6 µm, Yorkshire Bioscience) and a bacterial artificial chromosome (BAC) construct from chromosome 12 (RP11-125C7, 152 kbp, L=51.7 µm, position 12q21.31). The BAC contains an 11.6 kbp cloning vector (pBACe3.6). The DNA was dyed with YOYO-1™ fluorescent dye (Invitrogen) at a concentration of 1 dye molecule per every 5 base pairs. The running buffer consisted of 0.05×TBE (4.5 mM Tris, 4.5 mM boric acid and 0.1 mM EDTA) plus 10 mM NaCl, diluted with formamide (Sigma) to the volume fraction specified. In addition, we used an anti-photobleaching system consisting of a reducing agent, 3% % β-mercaptoethanol and an oxygen-scavenging system 4 mg/ml β-D-glucose, 0.2 mg/ml and 0.04 mg/ml catalase (added to loading buffer, which was then diluted with formamide). The single-molecule measurements were conducted with a fluorescence video-microscopy system incorporating a Nikon Eclipse TE2000 inverted microscope, 100×N.A. 1.4 oil immersion objective and an EMCCD camera (Andor, iXon and Photometrics Cascade II).

BAC Preparation

Bacterial Artificial Chromosome (BAC) clones were cultured in Luria-Bertani (LB) medium and 12.5 g/mL chloramphenicol at 37 C overnight in a shaking incubator. Then 1.5 ml of the culture was transferred to an eppendorf tube and spun down. The supernatant was discarded and the procedure was repeated with another 1.5 ml culture using the same tube. The pellet was resuspended in 250 µl of Pl buffer (50 mM TrisCl, pH 8.0, 10 mM EDTA, 100 µg/ml RNase A) and left on ice for 10 min followed by addition of 250 µl of P2 buffer (200 mM NaOH, 1% SDS (w/v)). The tube was then inverted 10-15 times and left on ice for 5 min. Next, 350 µl of P3 solution (3.0 M NaAc, pH 4.8) was added and the tube was inverted 10-15 times immediately and left on ice for 15 min. Then the tube was spun at 19800 g for 10 min at room temperature. The supernatant (approximately 850 µl) was transferred to a new tube, and treated with RNase A (15 µl; 10 mg/ml) at 37 C for 30-45 minutes. Following the phenol/chloroform extraction, the upper layer was transferred to a new tube. P3 buffer was added at volume of ⅛th of the transferred amount, followed by addition of cold isopropanol at a final concentration of 50%. The tube was inverted smoothly 10-15 times and placed in −80 C for a minimum of 30 minutes before being centrifuged at 4 C for 30 minutes. The supernatant was discarded and 1 ml of 70% alcohol was added. Following a 1 minute centrifugation, the alcohol was removed and the dried pellet was resuspended in 25-30 µl of distilled water.

DNA Loading Protocol

The molecules are brought from the microchannels into the nanochannels with a burst of high pressure (FIG. 8 a). The molecules introduced in the nanochannels are then concentrated in the nanogrooves via the following procedure. Equally distributed positive pressure is applied to the four reservoirs adjoining the nanochannels, forcing buffer to circulate through the nanochannels and out into the nanoslit (FIG. 8 a-b). This flow pattern will cause nanochannel confined molecules on either side of the nanoslit to be symmetrically driven into the nanogrooves. As the nanoslit region is more confined than the nanogrooves (FIG. 8 b), in order to escape from the nanogrooves into the nanoslit the molecules must cross through an entropic barrier. While at high enough pressure the flow will be sufficient to overcome the barrier, and molecules will be forced out of the nanogrooves, below a certain pressure threshold DNA will remain trapped in the nanogrooves. Consequently, for applied pressures below this threshold, the effect of the circulating flow will be to concentrate molecules in the center of the nanogroove array (FIG. 8 c). While it is possible to run the devices with only the initial loading step, the concentration protocol consistently maximizes the number of molecules available for imaging in the microscope field of view.

Time-Trace Rescaling

Once raw movies of denatured molecules are acquired, we normalize the time-trace plots of all molecules so that averaged single-molecule barcode profiles can be obtained. The first step is to align the molecule center-of-th mass across all frames. We accomplish this by using correlation of the i frame with th the initial frame to obtain the translational offset of the i frame relative to the initial frame. The second step is to 'smooth-out' longitudinal thermal fluctuations in the contour density that create a local distortion of the barcode structure. While using a single dilation factor to normalize the profiles works well, it is possible to improve the procedure by using local dilation/contraction factors. Thus, instead of using a single overall adjustment to normalize the molecule extension between plots, we use local adjustments, so that different positions along the molecule profile can receive different adjustments.

In practice we create a piece-wise linear map M, defined by a series of dilation factors $d_k$, the slopes of the individual linear components of the map (so that M is a function of the $d_k$, e.g. $M(d_k)$. The map $M(d_k)$ will then operate on the profile $P_i(x_j)$ at the $i^{th}$ frame to create a profile $P_i(x_j, d_k)$ ($x_j$ is the $j^{th}$ pixel of the profile). The parameters $d_k$ are chosen to minimize the least-squared difference $\Delta_i$ between the profile $P_i(x_j, d_k)$ and a template profile taken to be the profile at frame i=1 $P_1(x_j)P1(Xj)$):

$$\Delta_i = \sum_{j=1}^{N} (P_i(x_j, d_k) - P_1(x_j))^2$$

Figure 2:
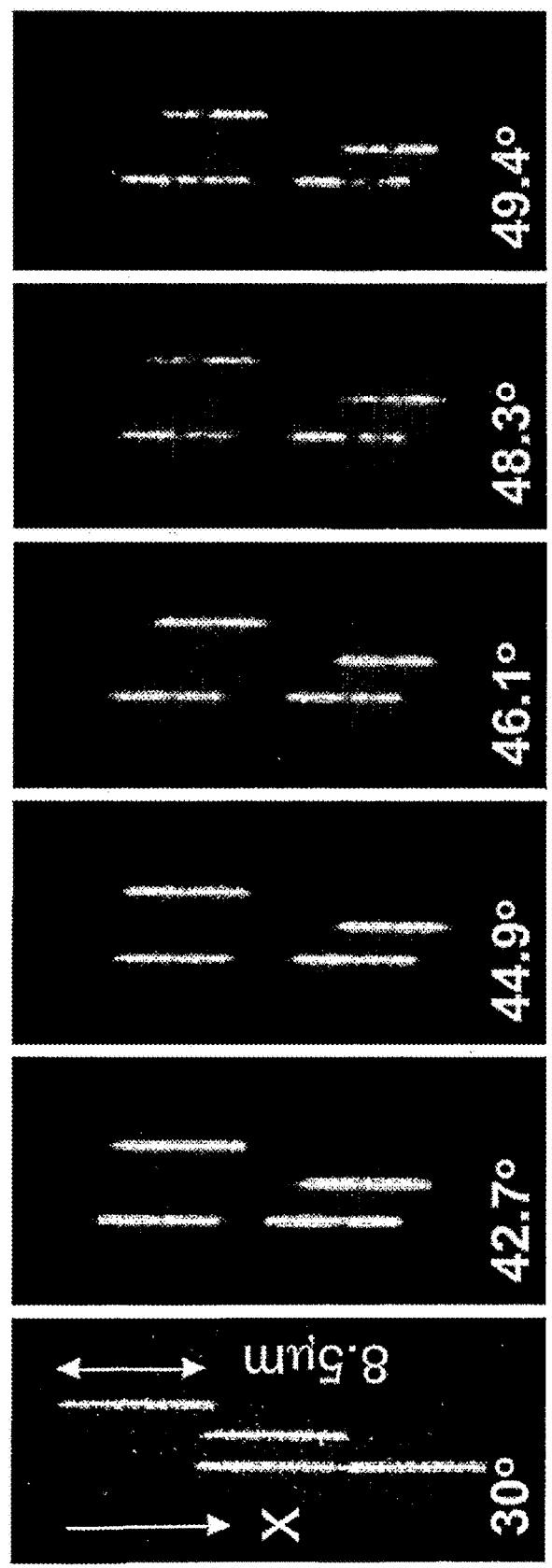
FIG. 2 shows lambda-phage DNA molecules imaged in a fluorescence microscope at different temperatures. The DNA molecules are shifted in position due to diffusion and drift.
Figure 3:
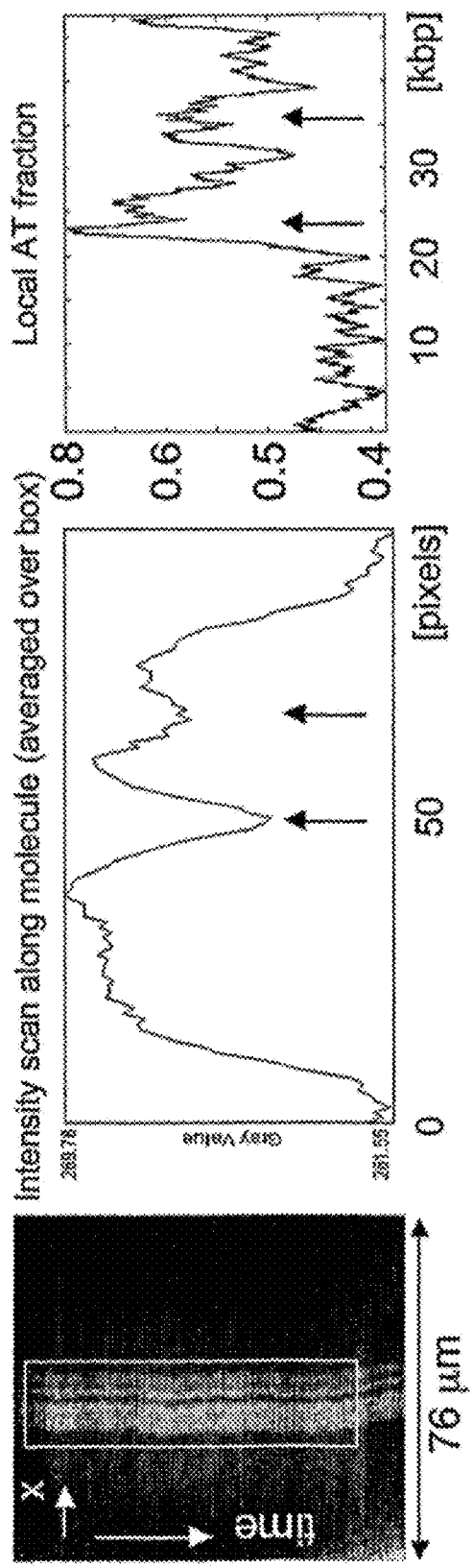
FIG. 3 shows (LEFT) Fluorescence image of one lambda-phage DNA molecule as a function of position and time, (CENTER) Average intensity of the rectangular selection to the left consistent with the graph to the (RIGHT) showing the known AT fraction (here calculated as the fraction of AT basepairs in a moving 300 bp window) along the lambda-DNA. Arrows highlight corresponding features in the intensity and AT fraction plots, respectively.

Using custom code written in Matlab, this procedure is applied to all frames, creating the rescaled time-series shown in Supplementary FIG. 2 a-b. Averaging over the rescaled frames we obtain the average barcode profile normalized to the local expansion/contraction present in the first frame.

We need, however, to obtain the average profile reflecting the true equilibrium conformation of the chain. This can be accomplished as follows: during the rescaling we save the maps $M_i(d_k)$ relating the profiles for each frame to the initial profile at frame i=1. From these saved maps we can compute the average map $\langle M(d_k) \rangle$: this map relates the true equilibrium profile to the profile at /=1. In order to correctly normalize the averaged rescaled profile to the true equilibrium chain conformation, we simply apply the inverse of this map ($\langle M(d_k) \rangle^{-1}$).

Barcode Alignment

In order to create a consensus barcode, it is necessary to align the profiles. The first step is to find the translational overlap and profile orientation that maximizes the correlation between a profile and a template profile. We then apply a global dilation to minimize the squared difference between the profile and template (as a precaution to avoid forcing agreement, we do not apply local dilation maps to align profiles taken for different molecules). The dilation accounts for any overall difference in the profile scaling, typically adjusting the relative scaling of the two profiles by less than 10%.

Barcode Registration with Theory

Figure 4:
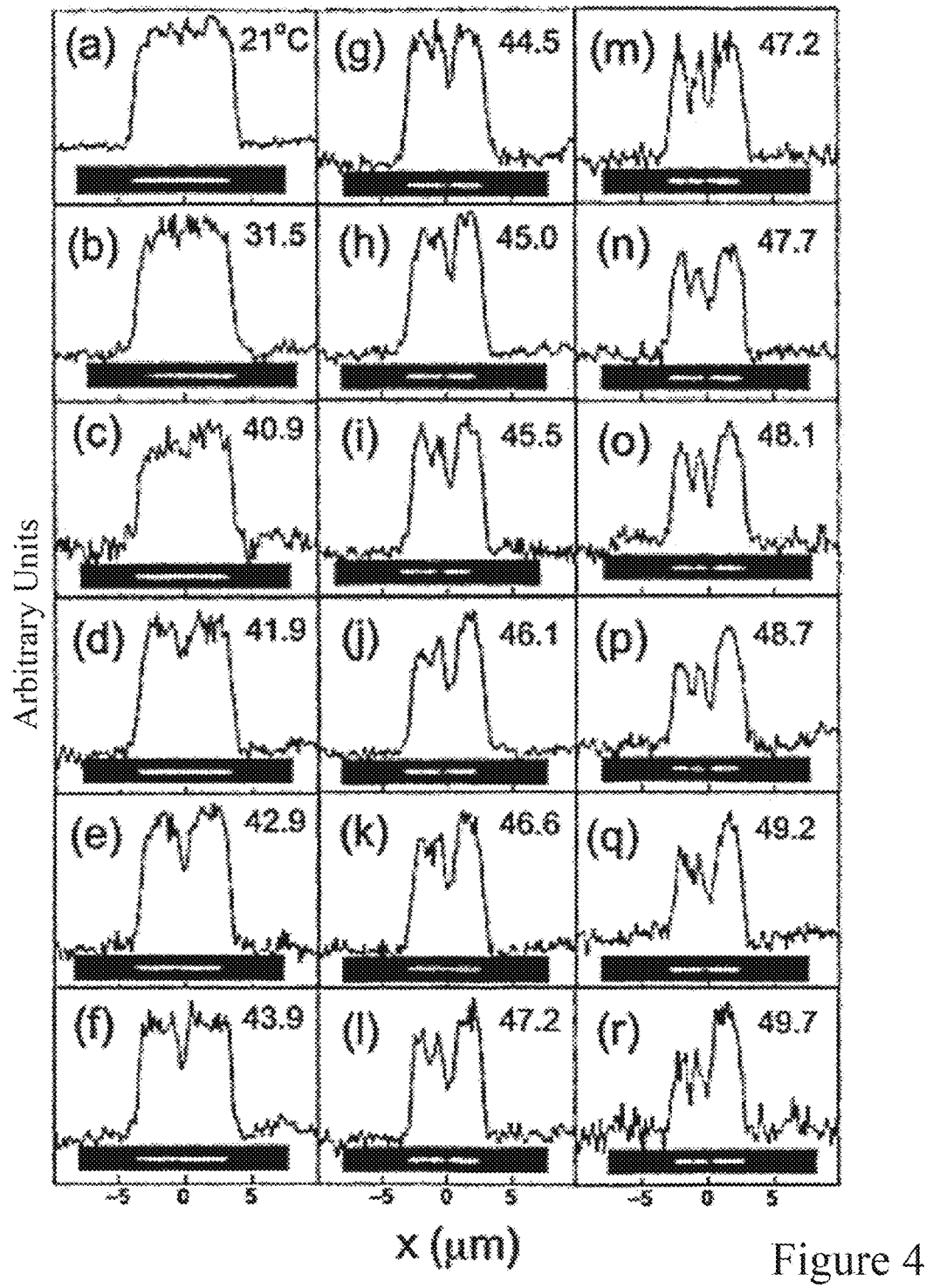
FIG. 4 shows fluorescence traces demonstrating melting of lambda-DNA in solutions of 0.05×TBE+ 10 mM NaCl with 33% formamide (by volume). The corresponding grayscale image of the molecule is displayed below the trace, (a)-(r) show fluorescence traces acquired for the same molecule in a thermal ramp cycle starting at 21° C.
Figure 5:
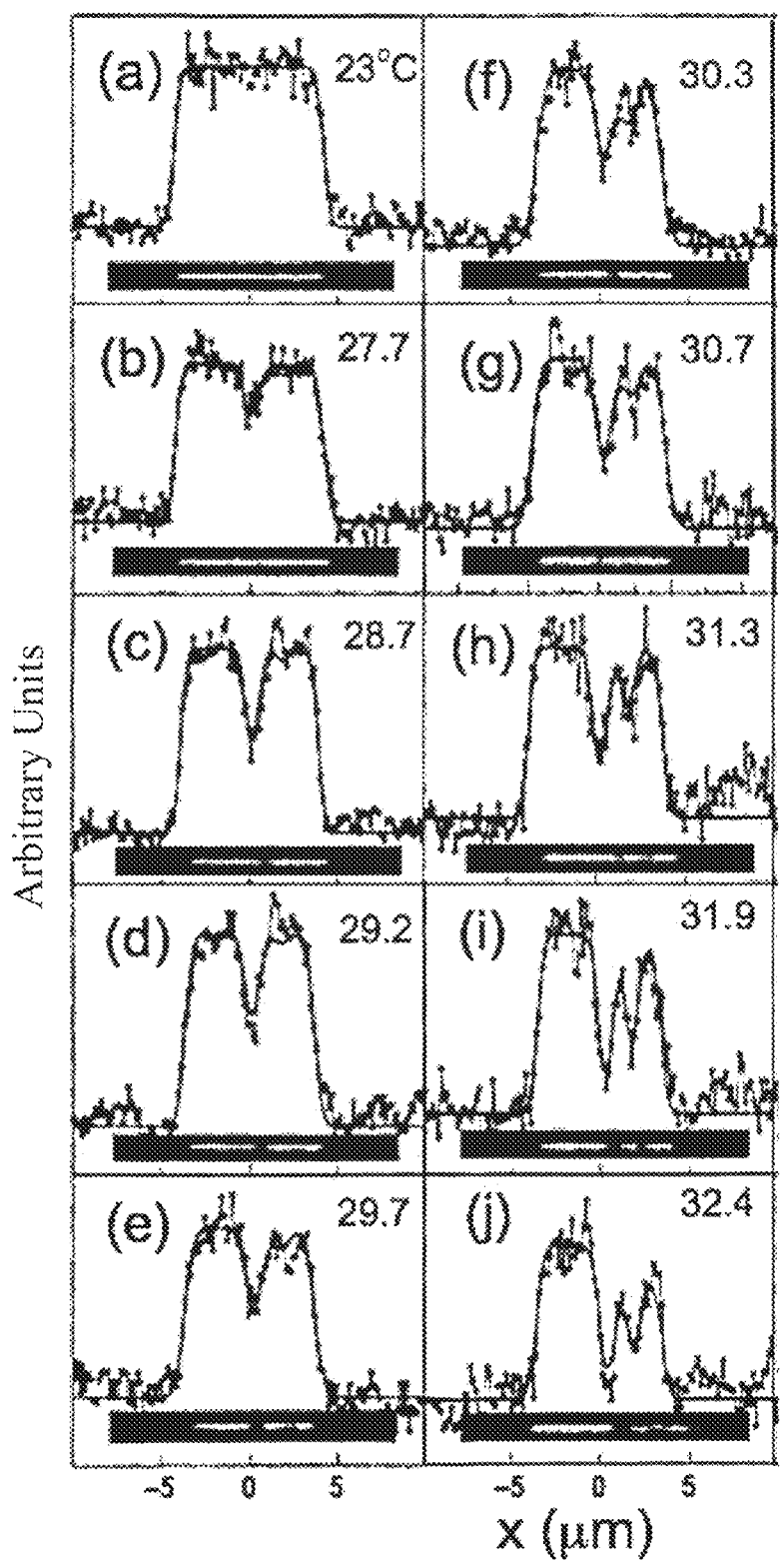
FIG. 5 shows fluorescence traces demonstrating melting of lambda-DNA in solutions of 0.05×TBE+ 10 mM NaCl with 50% formamide (by volume). The corresponding grayscale image of the molecule is displayed below the trace, (a)-(j) show fluorescence traces acquired for the same molecule in a thermal ramp cycle starting at 23° C.

In this procedure, the theoretical barcode is created using an extension per base pair estimated from the measured stretching of λ-DNA and a "best-guess" helicity. A single experimental profile is aligned to the theory using the method described above for aligning experimental profiles to experimental profiles (FIG. 4 cd). We term this experimental profile, aligned to theory, the "template". Additional experimental profiles are then aligned to the template to create a consensus barcode. We intentionally do not choose to align all the individual experimental profiles to theory in order to create a consensus profile that is based purely on alignments within the experimentally determined set of profiles. Lastly, we refine the theoretical profile by a least-squares fit of the theory to the aligned consensus profile, updating the "best-guess" helicity to a value determined via the secondary fitting procedure. If the template used to construct the consensus is correctly aligned to the theory, then the resulting consensus will also have the correct registration with the true sequence.

Global BAC Alignment

The global alignment of RP11-125C7 to the selected 10 Mbp region of chromosome 12 was performed automatically by finding the position of the BAC that minimized the least squared difference between the profile and the calculated genomic melting map. Let $P_T(x_j)$ be the theoretical profile and $P_{exp}(x_j)$ the experimental profile (with N pixels total). The estimator used was:

$$\Delta_i = \frac{\sum_{j=1}^{N} (P_T(x_{i+j-1}) - P_{exp}(x_j))^2}{\sum_{j=1}^{N} (P_T(x_{i+j-1}))^2}$$

the index i=1, . . . , n–N where n is the length of the calculated sequence. The measured stretching of λ-DNA was used to calibrate the correct dilation factor for the theoretical profile (variations of the dilation −10% did not change the global best fit position). The correct profile amplitude $I_O$, for generating the theoretical profile, was found by varying the amplitude and choosing the value $I_O$ that led to a global minimum of $\Delta(i, I_O)$, i.e. the amplitude that gives the best least-squares fit of theory to experiment.

Sequences and Melting Probability Profiles

Sequences used were downloaded from the NCBI GenBank and the UCSC genome browser (Assembly hg17). In particular, the T4GT7 sequence was obtained from T4 by deletion of a 3.256 bp segment between site 165,255 and 168,510. Melting probability profiles were then calculated from the sequences using the website www.stitchprofiles.uio.no.

What is claimed is:

1. A method comprising:
   stretching a DNA segment at least 1 k base pairs long within a nanofluidic channel of a nanofluidic channel device and labelling the segment of DNA using an intercalating dye in the presence of DNA denaturation conditions; and
   mapping a feature of the stretched DNA.

2. The method according to claim 1, wherein
denaturing the DNA is achieved using at least one process selected from the group comprising:
   exposing the stretched DNA segment to a predetermined temperature;
   applying a chemical treatment to the stretched DNA segment; and
   changing buffering conditions of the DNA segment within the nanofluidic channel.

3. The method according to claim 1, further comprising driving the DNA segment into proximity of the nanofluidic channel by at least one of:
   a pressure differential within the nanofluidic channel device; and
   an electrical potential applied to a predetermined region of the nanofluidic channel of which the nanofluidic channel forms part.

4. The method according to claim 1, wherein
the fluorescent dye is a dimeric cyanine nucleic acid stain.

5. The method according to claim 1, further comprising applying predetermined mapping techniques and algorithms to generate a DNA segment profile using a set of optical fluorescence images acquired with the stretched, denatured, and labelled DNA segment in order to map nucleotide features within the segment of DNA, thereby generating a barcode of the sequence of a predetermined pair of base pairs within the DNA segment, wherein
the set of optical fluorescence images depict fluorescence variations along the DNA segment which are the result of either binding or unbinding of the fluorescent dye when the DNA denatures.

6. The method according to claim 5, wherein
the predetermined mapping techniques and algorithms comprise
   time-trace rescaling the set of optical images to generate single molecule barcode profiles by aligning the DNA segment profiles to a reference location and processing the DNA segment profiles based upon a first dilation process to filter out longitudinal thermal fluctuations in the DNA segment profiles; and
   creating a consensus barcode by aligning the single molecule barcode profiles by maximizing correlation of each single molecule barcode profile with a template profile and applying a second dilation process to account for differences in the profile scaling by minimizing a difference between each DNA segment profile and a template profile.

7. The method according to claim 6, wherein
generating the template profile comprises creating a theoretical barcode by using an extension per base pair derived from measured stretching of a DNA calibration standard of known size and an estimate of helicity and then aligning a measured single molecule barcode profile to the theoretical barcode.

8. The method according to claim 6, wherein
minimizing a difference comprises minimizing the squared difference.

9. The method according to claim 5, wherein
the barcode relates to localized AT and GC base pair ratios.

* * * * *